(12) United States Patent
Haylor et al.

(10) Patent No.: US 8,790,305 B2
(45) Date of Patent: Jul. 29, 2014

(54) INFUSION APPARATUS

(75) Inventors: Nicholas Bryant Haylor, Bracknell (GB); Simon Francis Everleigh, Chichester (GB); Rene Werner Ruedi, Farnborough (GB); Alexander Lloyd, Boston (GB); James Gower Johnson Shearn, Bidford-on-Avon (GB)

(73) Assignee: CareFusion 303, Inc., San Diego, CA (US)

( * ) Notice: Subject to any disclaimer, the term of this patent is extended or adjusted under 35 U.S.C. 154(b) by 5 days.

(21) Appl. No.: 13/346,675

(22) Filed: Jan. 9, 2012

(65) Prior Publication Data

US 2012/0156073 A1    Jun. 21, 2012

Related U.S. Application Data

(63) Continuation of application No. 11/632,583, filed as application No. PCT/GB2005/002747 on Jul. 13, 2005, now Pat. No. 8,118,778.

(30) Foreign Application Priority Data

Jul. 16, 2004   (GB) .................................. 0416006.5

(51) Int. Cl.
*A61M 5/00*   (2006.01)
(52) U.S. Cl.
USPC ............... 604/131; 604/151; 604/152; 604/2; 16/254
(58) Field of Classification Search
USPC .......... 604/29, 34, 67, 131, 151, 246; 16/254, 16/258, 259, 261, 262, 264, 266, 270
See application file for complete search history.

(56) References Cited

U.S. PATENT DOCUMENTS

| | | | |
|---|---|---|---|
| 4,399,030 A | * | 8/1983 | Hlavinka et al. ................. 210/91 |
| 2002/0165503 A1 | * | 11/2002 | Morris et al. ................. 604/250 |

FOREIGN PATENT DOCUMENTS

| | | |
|---|---|---|
| JP | A-59-501395 | 1/1985 |
| JP | A-62-221365 | 9/1987 |
| JP | A-6-299754 | 10/1994 |
| JP | A-7-313593 | 12/1995 |
| JP | A-9-217541 | 8/1997 |

OTHER PUBLICATIONS

Office Action for Japanese Patent Application No. 2007-520889 mailed Jul. 31, 2012.

* cited by examiner

*Primary Examiner* — Laura Bouchelle
(74) *Attorney, Agent, or Firm* — McDermott Will & Emery LLP (57) ABSTRACT

In a peristaltic medical infusion pump unit, comprising a peristaltic assembly and a counter surface or anvil facing said peristaltic assembly and provided by the inner surface of a door pivotally mounted on a housing of the unit, the door is readily non-destructively removable and replaceable. In use of the peristaltic pump unit, a flexible resilient tube forming part of a medical fluid delivery line is extended between the peristaltic assembly and the counter surface or anvil provided by the door. The medical fluid delivery line has first and second color coded fittings spaced therealong upstream and downstream of the peristaltic assembly and the region of the housing of the pump unit across which the infusion line is extended is provided, correspondingly spaced above and below the peristaltic assembly with correspondingly color coded support means for these fittings.

8 Claims, 11 Drawing Sheets

INFUSION APPARATUS

This application is a continuation of U.S. application Ser. No. 11/632,583, filed on Aug. 5, 2008 and now issued as U.S. Pat. No. 8,118,778, that is the U.S. national phase application of PCT/GB2005/002747, filed Jul. 13, 2005, which claims priority to United Kingdom patent application GB0416006.5 filed on Jul. 16, 2004, all of which are hereby incorporated by reference in their entirety.

THIS INVENTION relates to infusion apparatus for parenteral infusion of medical fluids to patients.

More particularly, the invention relates to infusion pump units for such infusion apparatus which units comprise a peristaltic pumping mechanism comprising a peristaltic pump in which a flexible resilient tube, forming part of a fluid delivery line for delivering a medical fluid to a patient is located between, on the one hand, a peristaltic assembly, for example, an array of displaceable fingers, and, on the other hand, a counter surface or anvil, said tube, in use of the apparatus, being repeatedly pressed against the anvil or counter surface, by said peristaltic assembly, at different positions along the flexible resilient tube in a predetermined sequence, to provide a peristaltic pumping action in a manner well known per se. In one known type of such apparatus, for practical reasons, a mechanism for driving a plurality of displaceable fingers to achieve the desired pumping action, and, typically, monitoring or sensing devices of one kind or another, are incorporated in a housing of the pump unit and said anvil or counter surface is provided by a door or cover hingedly connected with said housing, the arrangement being such that in an open position of the door, said anvil or counter surface is spaced from the pressure elements so that the way is clear for the introduction of a medical fluid line, incorporating such a flexible resilient tube, across said housing so that said flexible resilient tube forming part of said line is extended across the peristaltic assembly and so that the door can thereafter be swung into a closed position in which said flexible resilient tube is located between the peristaltic assembly and the anvil or counter surface, with the parts of the medical infusion line above and below said flexible resilient tubing extending freely from the pump unit, from between said housing and said door, at opposite ends of said door, the door being releasably securable in said closed position to retain said flexible resilient tube in place.

An infusion apparatus of the above kind and a pump unit of the above kind are herein referred to as being "of the kind specified".

In an infusion apparatus of the kind specified, it is generally desirable that the door should be capable of being occasionally, non-destructively detached from and re-fitted to the housing, for example to allow thorough cleaning of the housing and/or the door. It is one object of the present invention to provide an arrangement allowing for the detachment and replacement of such a door from and to such a housing in a straightforward manner.

According to one aspect of the invention there is provided an infusion apparatus of the kind specified wherein said door is readily non-destructively removable, e.g. for cleaning purposes, and replaceable and wherein the housing carries at least one journal and the door carries a complementary bearing arrangement, said bearing arrangement including a first part having an open-ended transverse slot terminating in a bearing surface for said journal and a second part moveable with respect to said first part and which in a first position discloses said transverse slot to allow said journal to pass transversely through said slot into co-operation with said bearing surface, said second part being moveable into a second position in which it obstructs such transverse slot and provides a further bearing surface co-operating with said journal. Preferably said first part and said second part each have an open-ended transverse slot terminating in the respective bearing surface the second part being rotatable between a position in which the transverse slots are in alignment to allow transverse passage of said journal into co-operation with said bearing surfaces and a second position in which said second part obstructs movement of the journal out of said first part.

In infusion apparatus of the kind specified, a further problem encountered is that hard-pressed nursing staff sometime attempt to arrange the infusion line in the pumping unit in the opposite direction from that intended, i.e. in such a way that operation of the peristaltic pump would tend to pump fluid from the patient towards the medical fluid source rather than in the intended direction. Various measures have been proposed in tile past to minimise the likelihood of nursing staff making this mistake but these measures have not been entirely successful. It is an object of another aspect of the invention to provide improved means of safeguarding against such a mistake.

According to this aspect of the invention, there is provided infusion apparatus of the kind specified in which the infusion line has first and second colour coded fittings spaced, therealong upstream and downstream of said flexible resilient flexible tube and wherein the region of said housing of the pumping unit across which the infusion line is to be extended is provided, correspondingly spaced above and below the peristaltic assembly, with correspondingly colour coded support means for said fittings.

A further problem may be encountered in relation to the operation of infusion apparatus of the kind specified, as follows. There are occasions, in medical treatment, for example in intensive care facilities, where it may be necessary to infuse a patient simultaneously with several different medical fluids, at respective different rates and so on. Furthermore, in, for example, intensive care facilities, there may be several patients in one room or ward in a similar condition. Typically, each such patient may have a respective infusion apparatus of the kind specified for each medical fluid being administered. State-of-the-art infusion apparatus of the kind specified generally incorporates sensors for sensing when something goes wrong with the infusion process and for activating an alarm when this occurs. Typically, the alarm will include an audible alarm and, for example, an alarm light on the housing of the pump unit concerned, which will flash to identify the pump unit associated with the alarm condition. Usually the pump unit will also trigger a nurse call, (i.e. send a signal along an appropriate communication channel to alert a nurse) when such an alarm conditions occurs.

According to another aspect of the invention there is provided a docking station for supporting a plurality of infusion pumps of infusion apparatus of the kind specified, said infusion pumps having respective output signal connectors, and wherein said docking station includes electronic processing means for receiving signals from said output signal connectors and further includes visual alarm signal means and information display means such that where a plurality of such infusion pumps are mounted on such docking station and connected with said processing means, and one of said infusion pumps produces an alarm signal, a corresponding output signal is provided to said processing means, causing the latter to activate said alarm means and to present, on said display means, an indication as to which of the pump units mounted on the docking station is generating the alarm.

According to a yet further aspect of the invention there is provided a pump unit of the kind specified in which at least one sensor, and a bracket arrangement for supporting a respective part of an infusion line, are incorporated in a module designed for ready fitting to the remainder of the apparatus. With this arrangement, it is possible for a manufacturer of infusion apparatus of various sizes and types, for example, to design these various apparatus in such a way as to receive the standard module, thereby facilitating manufacture and repair of the apparatus.

An embodiment of the invention is described below by way of example and with reference to the accompanying drawings in which:—

Figure 1:
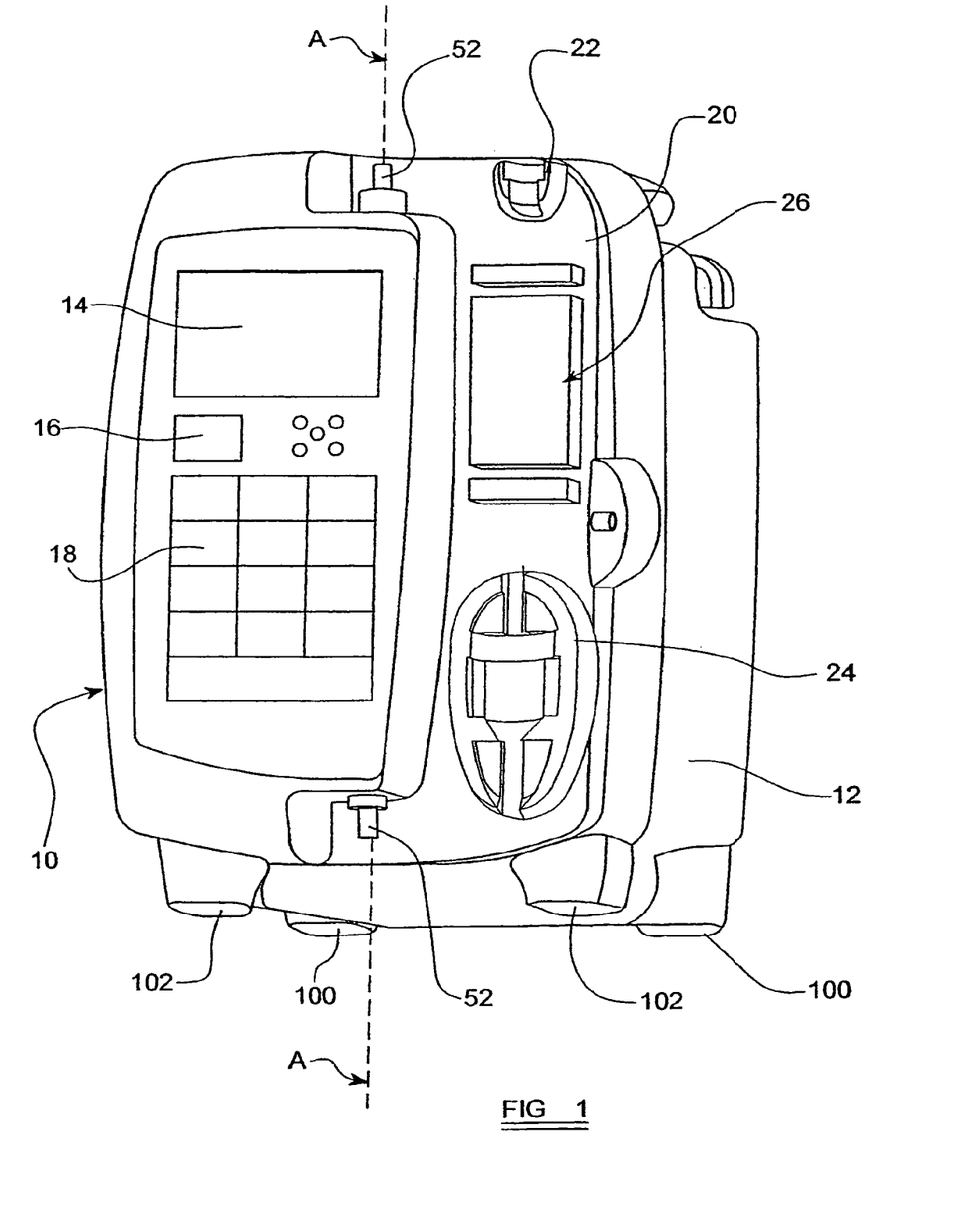
FIG. 1 is a perspective view showing an infusion pump unit embodying the invention, with a removable door removed.
Figure 2:
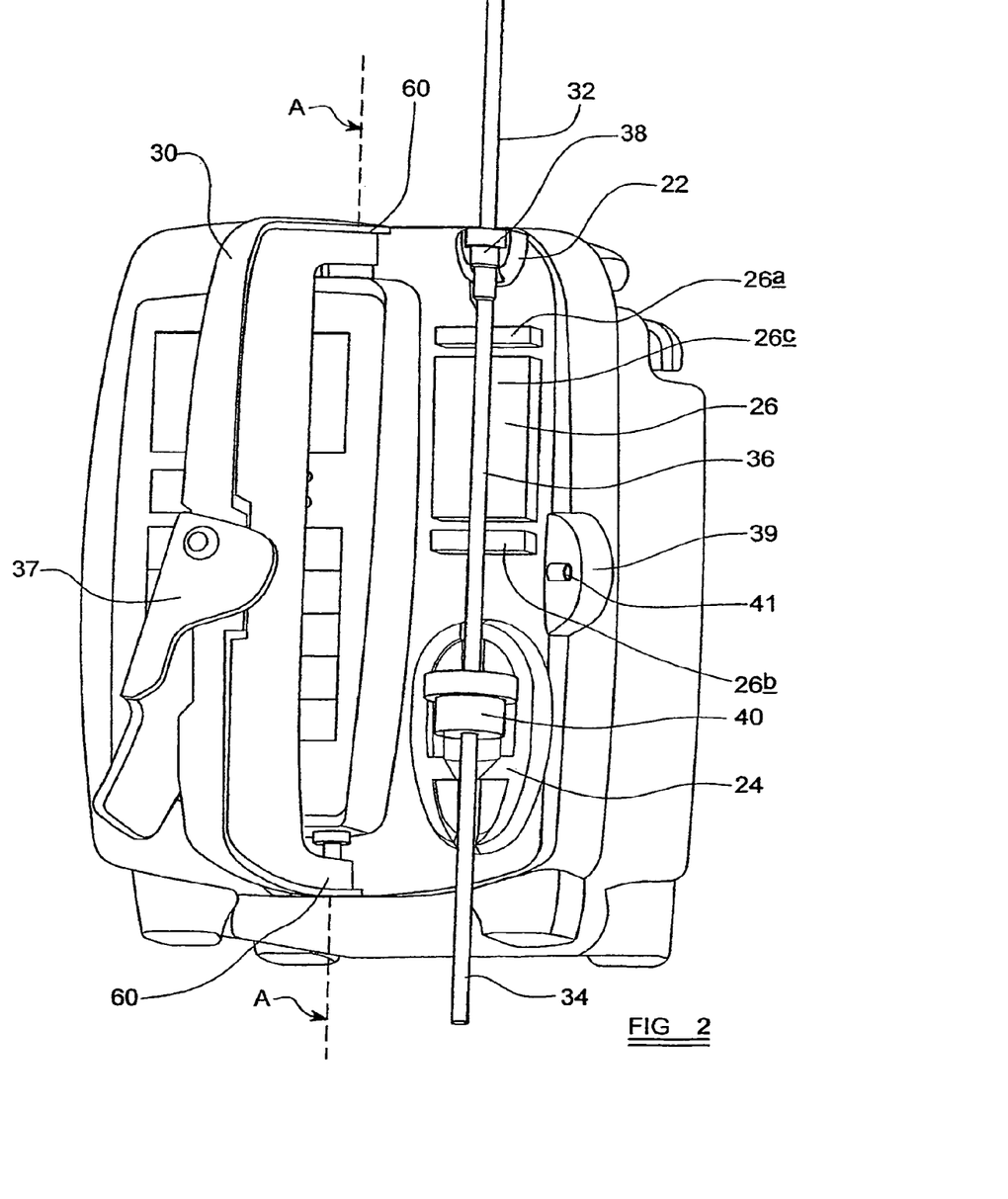
FIG. 2 is a corresponding perspective view showing the unit of FIG. 1 with the removable door in place and in an open position and further showing part of an infusion line in place.
Figure 3:
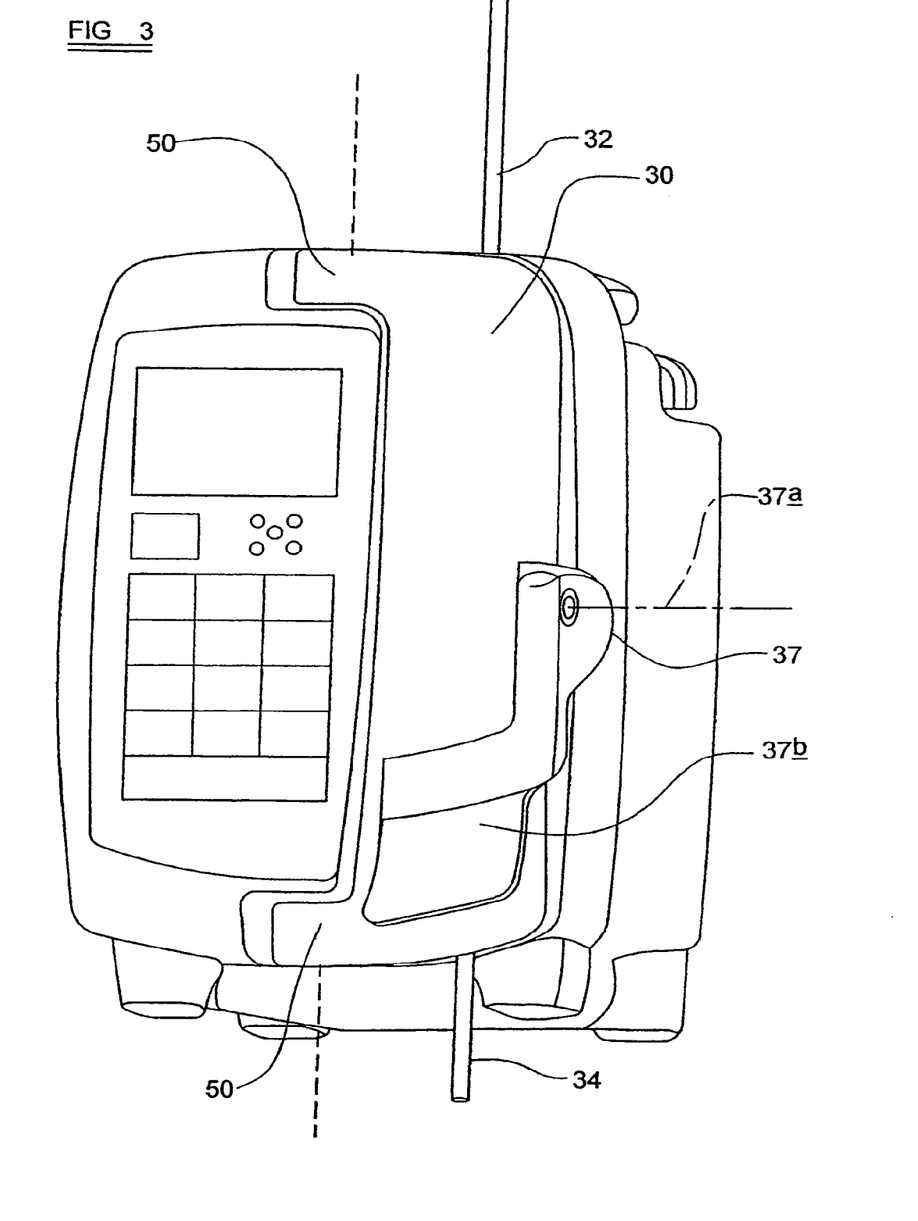
FIG. 3 is a perspective view of a pump unit of FIG. 2, complete with door, but with the door in a closed position in which the infusion line is held in the unit.

Referring to the drawings, and firstly to FIGS. 1 to 3, an infusion system for parenteral infusion of a medical fluid to a patient comprises a pump unit 10, a major part of which comprises a housing 12 which accommodates, in manner known per se, a cam mechanism controlling a plurality of fingers of a peristaltic pumping mechanism, an electric motor and associated gearing, driving said cam mechanism, and further accommodates electronic control and processing circuitry for controlling such motor and processing signals from pressure sensors etc. provided on the unit. The pump unit, as shown, may also comprise an electronically operated display 14, an alarm light 16, an input keyboard 18 or other manually operated controls, all in manner known per se. On its rear side (see FIG. 12) the housing 12 is provided with a channel 17 to receive a mounting rail or column, for example a mounting rail or column 124 (FIG. 11) of a docking station 126 whereby the pump unit may be readily fitted to or detached from such docking station. As illustrated in FIG. 12, the pump unit is also provided at its rear with a swing-down bracket 156 having a clamping screw 158 whereby the unit may be clamped to such vertical rail or column. The unit is also provided on its rear side with a horizontal channel 150 to fit over a horizontal supporting rail (e.g. of a docking station) and has a rotatable securing member 152 to secure such a horizontal rail in the channel 150. The rear of the unit 10 may likewise be provided with various connectors including connectors for receiving complementary power supply connectors, electronic communications interfacing connectors for providing data and alarm output signals and for receiving input signals, etc.

Figure 7:
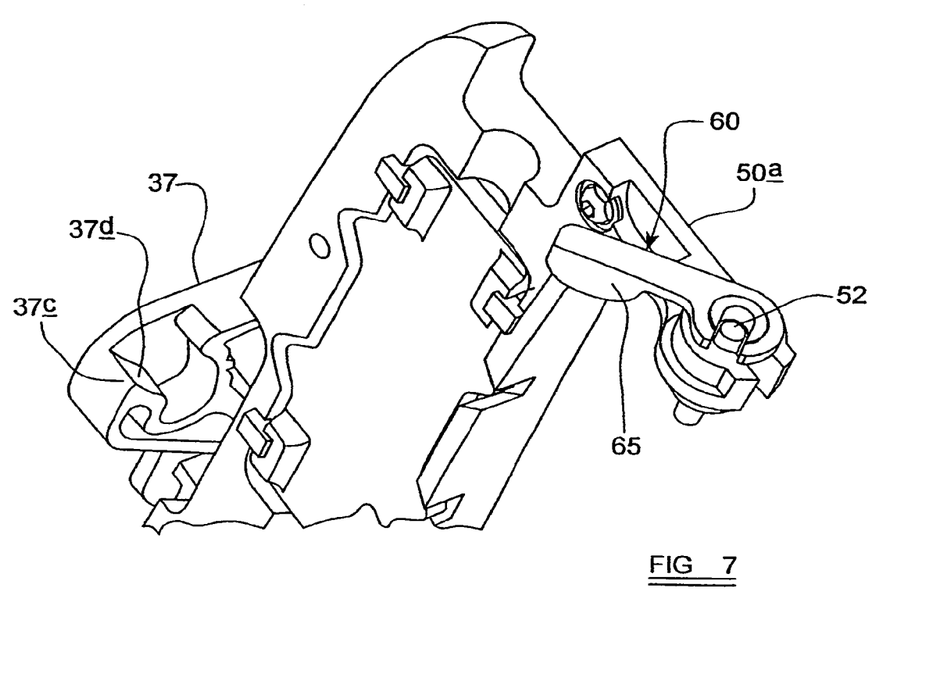

As shown in FIGS. 1 and 2, on the front of the housing there is provided a face or deck 20 on which is exposed an upper mounting or bracket 22 for a complementary fitting 38 forming part of an infusion line; a lower mounting or bracket 24 for a complementary fitting 40 forming part of such infusion line and a peristaltic assembly 26 which is, effectively, the operative end of the peristaltic pumping mechanism and may, in principle, be the free ends of respective fingers moveable, by the cam mechanism referred to, inwards and outwards from the face or deck 20. In order to make it easier to maintain sterile conditions, these fingers may be covered by a thin flexible membrane, (not shown), sealed at its edges with respect to the deck 20. As shown in FIGS. 2 and 3, a door 30 is normally fitted to the housing 12 and can be swung between an open position illustrated in FIG. 2 and a closed position illustrated in FIG. 3, about a pivotal axis A. A medical fluid infusion line, for use with the pump unit, comprises upper and lower sections 32 and 34 respectively of transparent plastics tubing, an intermediate section 36 of resiliently compressible tubing, for example of silicone rubber, and upper and lower fittings 38 and 40 via which the tubing section 36 is connected respectively with the upper line 32 and with the lower line 34. In use, the upper line 32 extends upwardly to a source of the medical fluid to be administered whilst the lower line 34 extends from the infusion pump to an infusion needle or the like inserted into the patient. In use, the infusion line is extended across the face or deck 20 of the pump unit so that the fittings 30 and 40 are received in the brackets 22 and 24 respectively and so that the tubing section 36 extends over the peristaltic assembly 26 as illustrated in FIG. 2. The infusion line is fitted in place in this fashion whilst the door 30 is in the open position shown in FIG. 2. After the infusion line has been so fitted, the door 30 is moved to the closed position shown in FIG. 3 and is secured by a catch 37 which comprises a lever mounted on the outer edge of the door 30 (i.e. the edge which lies at the side of the pump unit when the door is in its closed position), for pivoting about an axis 37a generally perpendicular to that outer edge of the door and parallel with the front face of the door. The catch 37 has a handle portion 37b which extends downwardly and partly across the front of the door and has a cam portion 37c adapted to fit within a complementary recess 39 at the front of the pump housing at the adjacent side of the pump, the cam portion 37c having a cam surface 37d, (see FIG. 7), configured to engage under a boss 41 (which projects laterally from the pump housing into recess 39) when, with the pump door 30 closed, the handle portion 37b is swung downwardly and rearwardly from a position in which it projects forwards and outwards from the door to a position (shown in FIG. 3) in which the handle portion 37b lies against the front of the door.

The pump housing may have a carrying handle, (not shown), pivotally mounted on top.

The terms "upper" and "lower" are used herein for convenience and should not be understood to mean that the apparatus must be used in the orientation shown in FIGS. 1 to 3. The unit will, of course, pump fluid perfectly well in any orientation.

In operation of the pump, in known manner, the fingers of the peristaltic assembly 26 periodically press the flexible resilient tubing against a counter surface or anvil to propel fluid within the infusion line along the latter. In the pump shown, the peristaltic assembly comprises an upper finger 26a and a lower finger 26b which are of a relatively limited extent in the longitudinal direction of the infusion line, and an intermediate finger or pad 26c, between the upper and lower fingers and which finger 26c is extended or elongated in the longitudinal direction of the infusion line. In operation, assuming the fluid is to be propelled downwards, as viewed in FIGS. 1 to 3, along the infusion line, the peristaltic assembly performs a repeating cycle in which, with the intermediate pad 26c spaced from the counter surface, the upper finger presses the flexible tube against the counter surface or anvil to close the tube at the location of the upper finger 26a, the lower finger is then withdrawn from the counter surface to open the tube at the location of the lower finger 26b, then the intermediate pad or finger 26c is moved towards the counter surface to drive the fluid in the tube adjacent the intermediate pad 26c downward along the tube, then the tube is pinched closed again between the lower finger 26b and the counter surface, then the upper finger 26a is withdrawn from the counter surface and the intermediate finger 26c withdrawn from the counter surface to draw fresh fluid into the part of the tube adjacent the intermediate finger 26c.

Figure 4:
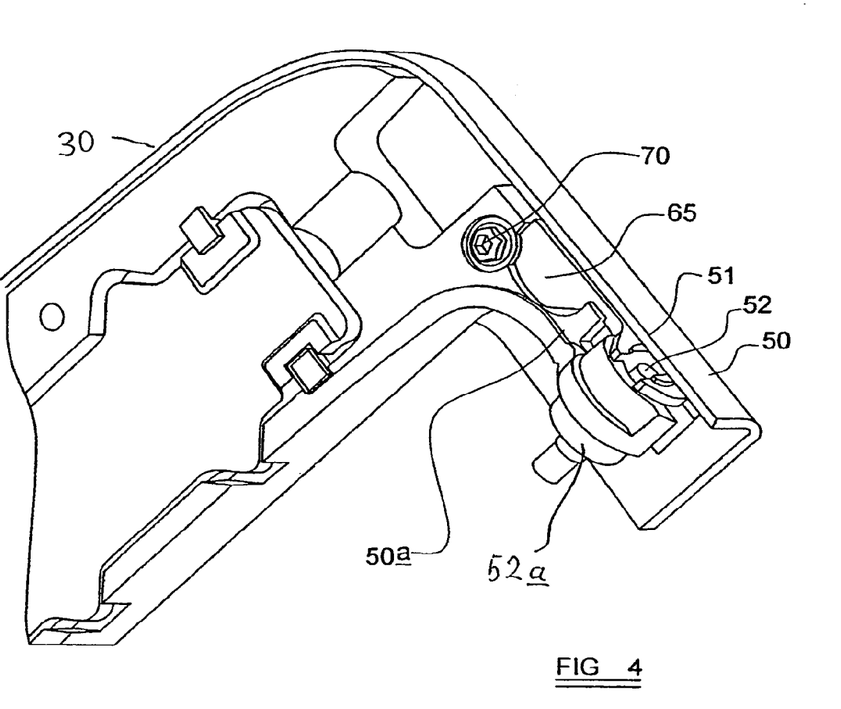
FIG. 4 is a fragmentary perspective view to an enlarged scale as compared with FIGS. 1 to 3 showing part of a hinge arrangement which allows ready removal of the door of the pump unit of FIGS. 1 to 3 when required.

In order for example, to allow for ready cleaning of the housing 12 or the door 30, or to allow ready replacement of the door 30 should the latter become damaged, means is provided in accordance with the present invention whereby the door 30 can be readily removed when required. As illustrated in FIGS. 4 to 7, the door has at its upper and lower ends laterally extending arms 50 which carry at their ends respective bearing arrangements for hinge pins or journals 52, fixed in the casing adjacent the upper and lower ends of the housing. The door comprises an inner part (shown partially in FIGS. 5 to 7), which provides the counter surface or anvil referred to, and an outer shell, (omitted in FIGS. 5 to 7 for clarity but visible in FIGS. 2, 3, 4 and 4a), secured to the outer side of the inner part. The portions of the inner part of the door which are incorporated in the arms 50 are referenced 50a in FIGS. 5, 6 and 7, and are referred to below as arms 50a. FIG. 4 is a fragmentary perspective view showing the upper part of the door 30, from the inside of the door, without the housing 12 but showing, in position in relation to the door, a unit 52a which is in practice fixed in the housing 12 and which provides the upper hinge pin or journal 52. (A corresponding unit fixed in the housing 12 likewise provides the lower hinge pin or journal 52).

Figure 5:
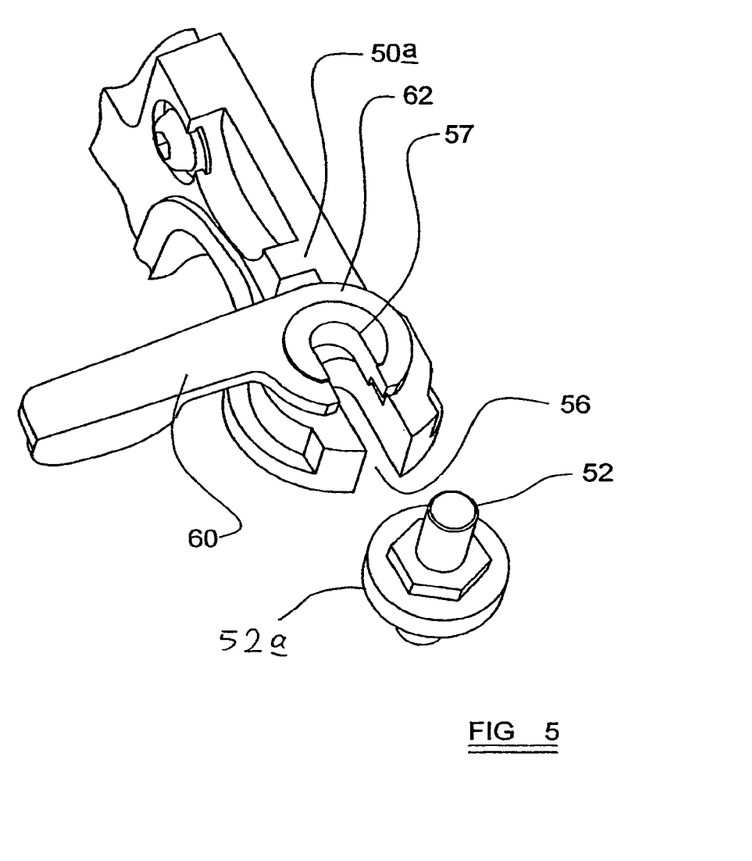
FIGS. 5, 6 and 7 are respective fragmentary perspective views of part of the door, illustrating the hinge arrangement.
Figure 6:
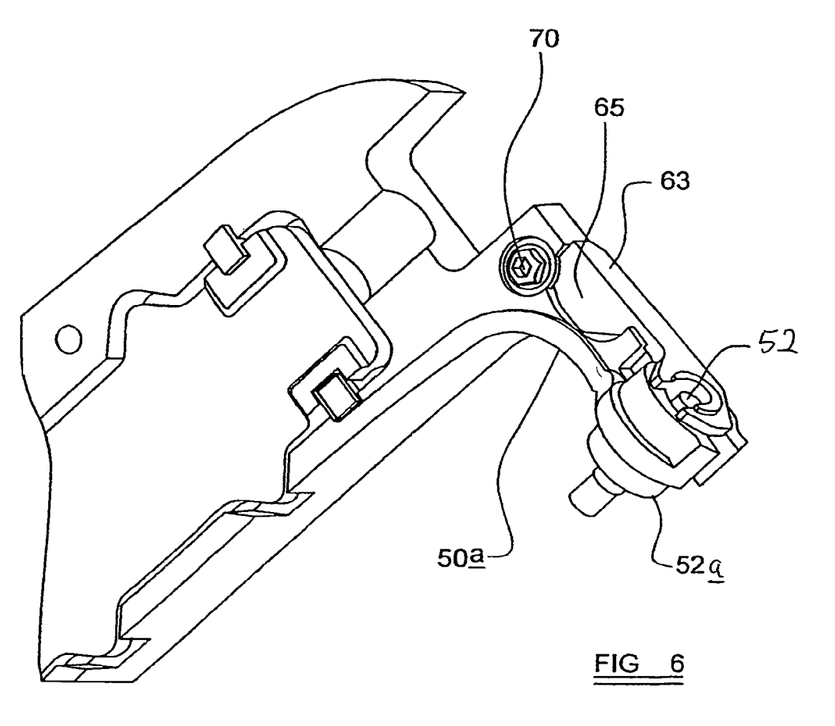

As best shown in FIG. 5, each said arm 50a (only one is shown, the other being a mirror image) has at one end a slot 56 extending to the end of the respective arm, the inner end of the slot being of semi-cylindrical form of a curvature corresponding to that of the bearing surface of hinge pin or journal 52. Rotatably mounted on the end portion of the arm 50a, for rotation about the axis of the semi-cylindrical end surface of the slot 56 is a respective retaining lever 60, a hub portion 62 of which is likewise provided with a slot 57 opening onto the periphery of the hub portion, the inner end of this slot likewise being a semi-cylindrical surface coaxial with that of the semi-cylindrical surface of the slot 56 and of the same curvature. In the arrangement shown, the lever 60 on the upper arm 50a lies on top of the latter as viewed in FIGS. 1 to 3 (and conversely the corresponding lever 60 for the lower arm 50a (not shown) lies below the lower arm 50a). Each lever 60 is retained between the respective arm 50a and the opposing side wall 51 of part of the outer shell which lies in the respective arm 50 of the door, the hub 62 of the lever 60 having, on its side facing the arm 50a, a part-cylindrical boss which is received in a corresponding part-cylindrical recess on the adjoining side of the arm 50a, such boss and recess being again coaxial with the half-cylindrical surfaces at the inner end of the slot 56 and of the slot 57 in the lever 60, whereby the lever 60 is rotatably mounted on the arm 50a. The lever 60 is kept in place, when the door is removed, as described below, between the arm 50a and said side wall 51. In the position of the lever 60, (relative to the door and arm 50a) shown in FIG. 5, the transverse slots 56, 57 in the arm 50a and the lever hub 62 are aligned, defining a single open slot which, when the door is applied to the casing, can receive the respective hinge pin or journal 52. The lever 60 may then be swung through 90° to the position shown in FIG. 6 in which the slot 57 in the hub 62 is displaced through approximately 90° with respect to the slot 56 so that whilst the respective half-cylindrical ends of these slots co-operate with respective portions of the cylindrical part of the hinge pin 52, one side wall of the slot in the hub 62 obstructs the slot 56 and provides a bearing surface for engagement with the hinge pin 52 and likewise one side wall 56 of the slot 56 obstructs the slot 57 in the hub 62 so that the combination of the arm 50a and lever 60 retains the hinge pin 52 securely but is nonetheless rotatable around the hinge pin 52. In this, the closed position of the lever 60, the latter lies snugly against the arm 50a as shown in FIG. 6. More particularly, the lever arm of lever 60 may, as shown, comprise a major part 63 in the form of a wall or strip lying in the plane of movement of the lever arm and may further comprise a tab portion 65 extending at right angles to said part 63 and which, in said closed position of the lever, lies within a corresponding recess in the respective arm 50a of the inner part of the door. In this closed position of the lever, the part 63 lies snugly against the arm 50a between the arm 50a and the wall 51 of the outer shell. When the door is to be removed, both levers 60 are pivoted in the door to the position shown in FIG. 5 and the door is then pulled away from the pump housing and hinge pins. Door replacement is by the reverse of this procedure, the levers 60 finally being pivoted to the position shown in FIG. 6 to retain the door on the hinge pins 52.

Figure 4A:
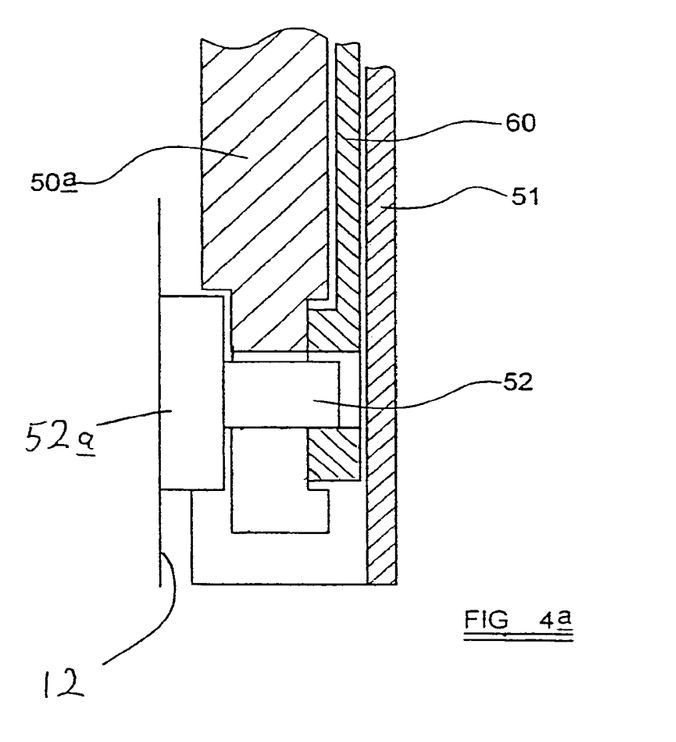
FIG. 4a is a view in section of a detail of the hinge arrangement.

FIG. 4a is a fragmentary sectional view showing the part of the door with the upper arm 50a, and also showing the unit 52a providing hinge pin 52 and indicating the part of housing 12 in which it is fixed. The section in FIG. 4a is taken in a plane through the axis A of the hinge pins 52 and which is generally parallel with the major surfaces of the door, and is taken with the lever 60 in the position shown in FIGS. 4 and 6 in which the respective hinge pin 52 is held captive in the arm 50a. Thus, the plane of section in FIG. 4a runs along the slot 56 in the arm 50a and through the open end of slot 56 and runs across the slot 57 in the lever 60.

In order to prevent inadvertent or unnecessary removal of the door by nursing staff or others, whilst still allowing ready removal and replacement of the door by servicing personnel, the levers 60 may be held in their closed positions by screws 70 screwed into the door inner part and the heads of which screws 70 overlie the tab portions 65 in their recesses and which screws must be undone to allow the levers 60 to be swung into their open positions. To facilitate mounting of the door and as a "backup" should a screw 70 become lost, the levers 60 and arms 50a may be provided with integral complementary retaining means, e.g. in the form of detents and co-operating recesses, or (less preferably) the levers 60 may have detents or recesses on the sides of parts 63 facing the respective walls 51 and co-operating with complementary recesses or detents on the walls 51 facing the parts 63.

Referring to FIGS. 1 and 2, the brackets 22 and 24 project forward somewhat from the face 20 and provide, or incorporate, respective resilient clips which define respective recesses to receive the respective fittings 38 and 40 of the infusion line, and these recesses are so shaped as to ensure, as far as possible, that the fitting 40 will not fit in the recess in bracket 22, nor will the fitting 38 fit in the recess in bracket 24. Likewise, the fittings 38, 40 and the brackets 22, 24 are so shaped as to ensure that neither fits in its respective bracket in an inverted position. Nevertheless, it has been found that, despite such measures, nursing personnel often take a significant time, if unfamiliar with a particular pump unit, to determine on a trial and error basis, the correct orientation and position of the infusion line in a peristaltic pump unit. Time may, of course, be very precious in a medical emergency situation. In accordance with the present invention therefore, to assist nursing personnel in quickly determining the correct orientation and position of the infusion line in the pump unit, colour coding is used. Thus the bracket 22 and fitting 38 are made of the same, visually striking, colour, distinct from the remainder of the pump unit and infusion line, and the bracket 24 and fitting 40 are made of the same visually striking colour as each other, but contrasting with that of the bracket 22 and fitting 38 and again distinct form the remainder of the pump unit or infusion line. For example, bracket 22 and fitting 38 might be blue and the bracket 24 and fitting 40 might be orange.

Referring to FIGS. 1 and 2 once more, the bracket 24, besides serving to co-operate with and hold the fitting 40 of the infusion line, also incorporates various sensors, such as a pressure sensor (not shown) of a type known per se, for measuring the pressure at which the medical fluid is supplied to the patient and a bubble detector, also known per se. A bracket performing the above-noted function and incorporating such sensors is likely to be required in any of a range of different infusion pumps of the character concerned. In the preferred embodiment of the invention, the bracket 24, the sensors referred to and possibly other facilities such as a mechanism for pinching off the infusion line when the door 30 is opened, are all incorporated in a module which can be easily fitted to the pump during manufacture, e.g. which can be simply "plugged in". Where the manufacturer produces a range of different models of pump unit, the different models are preferably designed to receive the same design of module, thereby rationalising manufacture to some extent, minimising manufacturing costs and stock-holding requirements for spares.

Figure 8:
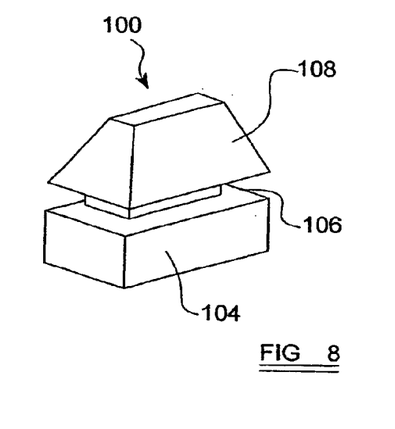
FIGS. 8 and 9 are perspective views of feet of the pump unit.
Figure 9:
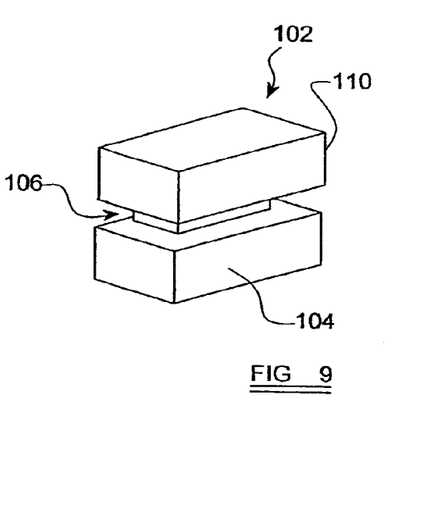
Figure 13:
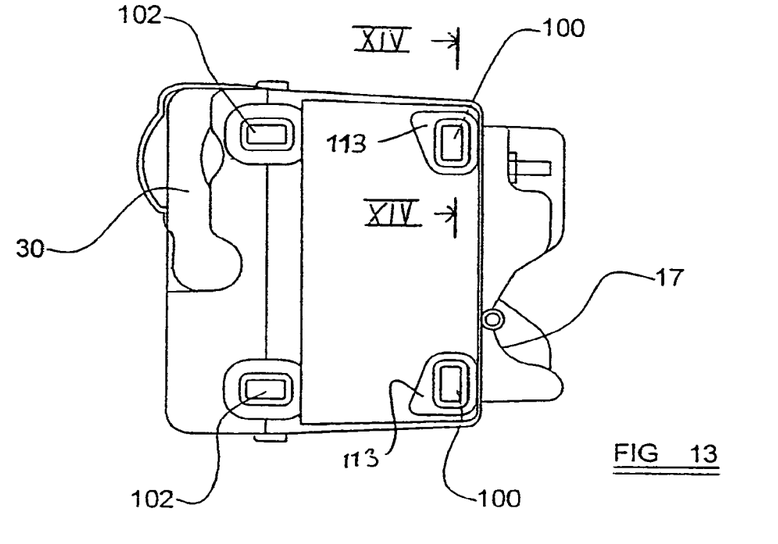
FIG. 13 is an underneath plan view of the pump unit.
Figure 14:
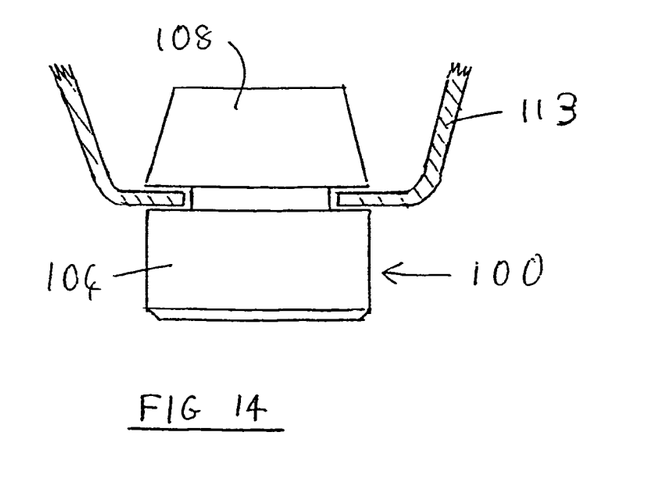
FIG. 14 is a fragmentary view in vertical section along the line XIV-XIV of FIG. 13.

The pump unit housing is provided with feet 100, 102, for example of elastomeric material, for use when the unit is to be supported on a flat surface rather than, for example, clamped to a rail. In prior infusion pump units, where the feet have simply been attached by adhesive to the bottom of the pump housing, these feet have had a tendency to become dislodged. Attachment of such feet to the bottom of the housing by screws has also proved unsatisfactory in that such screws are sometimes over-tightened during assembly causing the housing to crack. In the preferred embodiment of the invention, the feet used are unitary elastomeric items such as illustrated in FIG. 8 or FIG. 9 and which are inserted through holes in the bottom of the housing. Thus, each foot shown has a lower part 104, intended to be extended from the pump casing, a circumferential groove or rebate 106, intended to receive the edge of the hole in wall of the pump casing through which the foot is extended, and an enlarged retaining portion 108 (for foot 100) or 110 (for foot 102) above the groove 106 which engages the inside of the pump housing, to retain the foot against displacement from the hole. In the preferred embodiment of the invention, the pump unit has two rear feet 100 fitted in holes in downwardly projecting parts 113 of the pump housing, (see FIGS. 13 and 14) these feet each having an upper inner part 108 with a tapering wall to assist in pushing through the respective hole in the bottom of the pump housing. The pump housing, in the preferred embodiment, is formed in two parts, one providing a front panel of the housing and forward parts of the top, bottom and side walls, and the other part providing a back, and rearward parts of the side walls, top wall and bottom wall. The holes in which the front feet 102 are fitted are intersected by the junction between the front and rear housing parts so that the rear part of the housing has, in the forward edge thereof, at the bottom, two notches, corresponding to the rear parts of the respective holes for feet 102, into which the narrower parts, (defined by grooves 106), of feet 102 can be fitted before the front housing part having corresponding notches in its rear edge, at the bottom, is applied to the rear housing part, whereby the edge portions of the last-mentioned notches engage in the grooves 106 and holes encompassing the feet 102 are thus completed. In this way, the front feet 102, like the rear feet 100, are firmly and reliably held in place.

Figure 10:
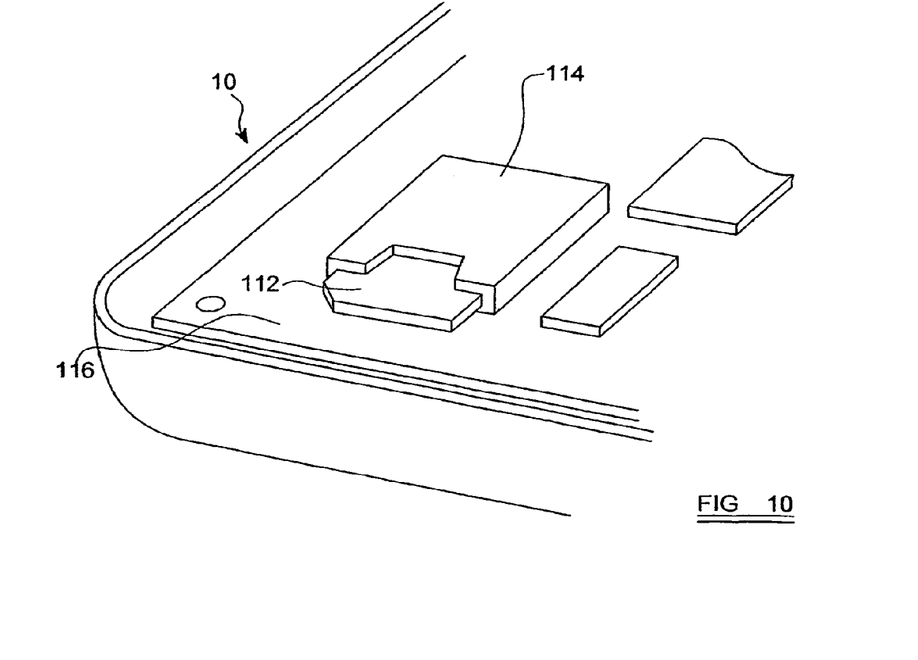
FIG. 10 is a fragmentary perspective view of part of the interior of the pump unit showing a Smart Media card mounted on a circuit board of the pump unit.

As noted above, the pump unit includes electronic processing means controlling operation of the motor driving the peristaltic assembly 26; receiving signals from the pressure and other sensors; receiving input from the keypad on the front of the pump unit; controlling the alarm means and the display; and so on. The electronic processing means comprises, in manner known per se, a CPU (central processing unit), running a program stored in electric memory within the pump unit. In preferred embodiments of the invention, this memory or a part thereof, is carried in a commercially available, readily replaceable, non-volatile memory card, such as a "Smart Media" card, a "Compact Flash" card, an "SDM" card or the like, received in a complementary socket within the pump unit, whereby the operating program of the CPU, or some aspect thereof, or pre-set data utilised by such program, may readily be changed, for example to provide for different medication administration regimes or improved control algorithms, simply by opening the pump unit housing, and exchanging cards. FIG. 10 illustrates such a "Smart Media" card 112 in a socket 114 mounted on a circuit board 116 within the pump unit 10.

At the rear of the casing, as shown in FIG. 12, are provided various electrical connectors, including a power supply connector 118 and data connectors. In the preferred embodiment, one of these data connectors may be a multi-pin connector, such as an RS232 connector 120 in which pins unused for data communication have been set aside for a nurse call function. As usual, a pump alarm will trigger the nurse call.

Figure 11:
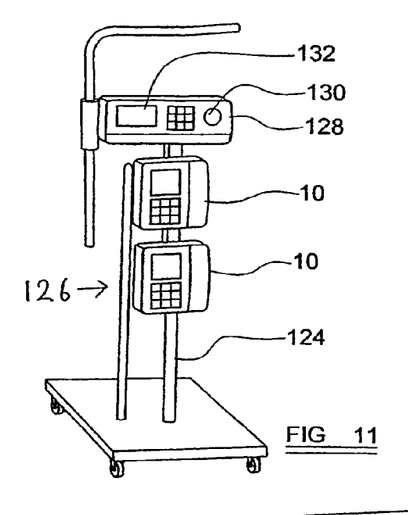
FIG. 11 is a perspective view of a docking station supporting several pump units.
Figure 11A:
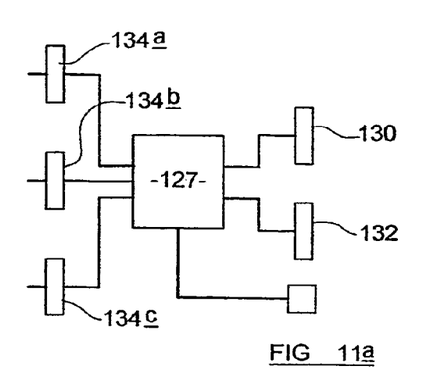
FIG. 11a is a schematic diagram of circuitry of a processing unit of the docking station.
Figure 12:
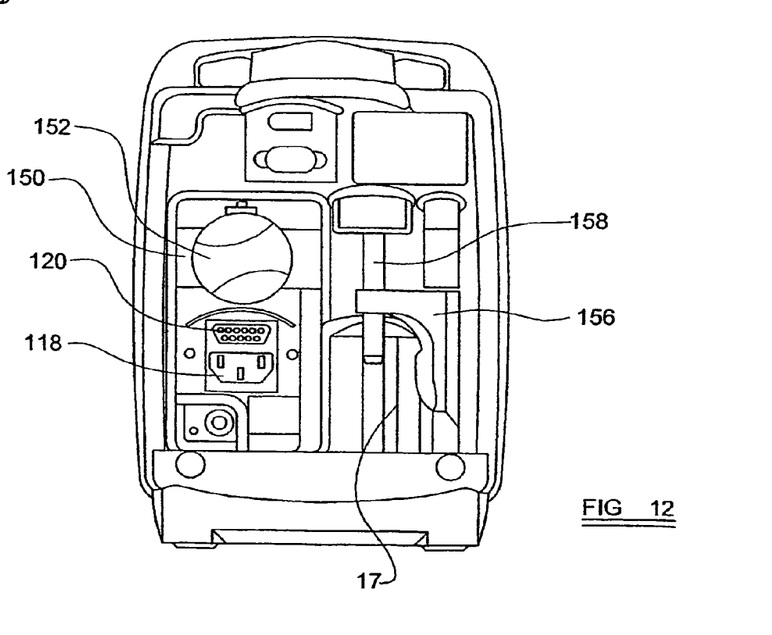
FIG. 12 is an elevation view of the fear of the pump unit showing an RS232 connector provided thereon.

Referring to FIG. 11 a plurality of pump units 10 may be mounted on a docking station 126 which may be located at the bed side of a patient being infused with respective medical fluids via the respective pumps 10 mounted on the docking station. The docking station includes electronic processing means 127 (FIG. 11a) housed in a unit 128 of the docking station which carries visual alarm signal means such as a lamp or beacon 130 and information display means 132 controlled by the electronic processing means in the unit 128. Respective output signal connectors of the pump units are connected with respective inputs 134a, 134b, 134c of unit 128. In operation, if one of the infusion pumps on the docking station produces an alarm signal, a corresponding output signal is provided via the respective input 134 to the processing means 127, causing the latter to activate the alarm means 130 and to present, on display means 132, an indication as to which of the pump units mounted on the docking station is generating the alarm. A nurse alerted by the alarm can thus readily and quickly determine which docking station 126 has the pump unit 10 associated with the alarm condition.

When used in this specification and claims, the terms "comprises" and "comprising" and variations thereof mean that the specified features, steps or integers are included. The terms are not to be interpreted to exclude the presence of other features, steps or components.

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be utilised for realising the invention in diverse forms thereof.

The invention claimed is:

1. A peristaltic pump unit for medical infusion, the peristaltic pump comprising:
   a housing comprising at least one journal or hinge pin;
   a peristaltic assembly coupled to said housing;
   an anvil coupled to said housing, the anvil facing said peristaltic assembly;
   a support means coupled to said housing, said support configured to support, between said peristaltic assembly and said anvil, a flexible resilient tube forming part of a medical fluid delivery line that further comprises first and second colour-coded fittings spaced therealong upstream and downstream of said flexible resilient flexible tube, the support means comprising correspondingly colour-coded first and second brackets configured to respectively accept said first and second colour-coded fittings;
   a driving mechanism coupled to said housing, the driving mechanism operable to drive said peristaltic assembly to pinch said flexible resilient tube against said anvil at different positions along the flexible resilient tube; and
   a door comprising a bearing assembly configured to couple with the at least one journal or hinge pin of the housing such that when the door is in a closed position, the flexible resilient tube is positioned between said peristaltic assembly and said anvil, the bearing assembly comprising (i) a first part, fixed relative to the door, having an open-ended transverse slot terminating in a bearing surface that is arcuate about an axis and (ii) a second part, moveable relative to the first part, which in a first position permits insertion of said at least one journal or hinge pin into said transverse slot and in a second position obstructs said transverse slot and provides a further bearing surface cooperating with said at least one journal or hinge pin;
   wherein the second part comprises a cylindrical boss partially extending about said axis, said boss being journaled in a recess provided in a face of the first part, which recess is also cylindrical and extends partially about said axis, and wherein said at least one journal or hinge pin is coaxial with said bearing surfaces when the door is positioned on the housing.

2. The pump unit of claim 1, wherein:
   said first colour-coded fitting comprises a first form and a first colour;
   said second colour-coded fitting comprises a second form that is different from the first form and a second colour that is different from the first colour;
   said first bracket comprises a first recess configured to accept said first colour-coded fitting and a color corresponding to the color of said first colour-coded fitting;
   said second bracket comprises a second recess configured to accept said second colour-coded fitting and a color corresponding to the color of said second colour-coded fitting; and
   the first and second recesses are further configured to resist the first colour-coded fitting being fitted in the second recess and to resist the second colour-coded fitting being fitted in the first recess.

3. The pump unit of claim 2, further comprising:
   at least one sensor coupled to said housing.

4. The pump unit of claim 2, wherein the first and second brackets comprise resilient clips configured to embrace their respective colour-coded fittings.

5. The pump unit of claim 3, further comprising a module configured to be fitted to the housing, the module comprising said second bracket and said sensor.

6. The pump unit of claim 5, wherein the module further comprises a mechanism for pinching off the medical fluid delivery line when said anvil is moved away from said peristaltic assembly.

7. The pump unit of claim 3, wherein said sensor comprises a pressure sensor.

8. The pump unit of claim 3, wherein said sensor comprises a bubble detector.

* * * * *